United States Patent [19]

Desai

[11] Patent Number: 4,490,355

[45] Date of Patent: Dec. 25, 1984

[54] BETAINE BASED COSMETIC FORMULATIONS

[75] Inventor: Bharat B. Desai, Belle Mead, N.J.

[73] Assignee: Miranol Chemical Company, Inc., South Brunswick, N.J.

[21] Appl. No.: 475,130

[22] Filed: Mar. 14, 1983

[51] Int. Cl.$^3$ ................ A61K 7/06; A61K 47/00; C11D 1/94

[52] U.S. Cl. .................... 424/70; 424/358; 252/545; 252/DIG. 5

[58] Field of Search .............. 252/546, DIG. 5; 424/70, 358

[56] References Cited

U.S. PATENT DOCUMENTS

| | | | |
|---|---|---|---|
| 3,328,307 | 6/1967 | Schmitz | 424/44 X |
| 3,755,559 | 8/1973 | Hewitt | 424/70 |
| 3,876,563 | 4/1975 | Collins | 252/545 |
| 3,980,769 | 9/1976 | Ghilardi et al. | 424/78 X |
| 4,110,263 | 8/1978 | Lindemann et al. | 252/545 |
| 4,233,192 | 11/1980 | Lindemann et al. | 252/545 |
| 4,329,334 | 5/1982 | Su et al. | 424/70 |
| 4,375,421 | 3/1983 | Rubin et al. | 252/DIG. 5 X |

OTHER PUBLICATIONS

McCutcheon's Detergents & Emulsifiers, 1978 Annual, p. 227.

Primary Examiner—Robert J. Warden
Assistant Examiner—Shawn P. Foley
Attorney, Agent, or Firm—Ladas & Parry

[57] ABSTRACT

A mixture of cocoamidopropyl betaine and oleamidopropyl betaine is included in cosmetics to improve thickening and foam boosting properties.

7 Claims, No Drawings

BETAINE BASED COSMETIC FORMULATIONS

BACKGROUND OF THE INVENTION

This invention relates to thickeners and foam boosters for use in cosmetics such as hair and skin care formulations.

Betaines are known in general as thickeners and foam boosters in hair and skin care formulations, such as shampoos and soaps. An example of such known betaine is MIRATAINE® ODMB-35 which is an oleyl betaine derived from dimethyl-oleyl amine. This betaine has good thickening properties but is a gel and is therefore difficult to work with. An object of the invention is to avoid such handling difficulties while still maintaining thickening and foam boosting properties by use of specific betaine compositions.

SUMMARY OF THE INVENTION AND DESCRIPTION OF THE PREFERRED EMBODIMENTS

The invention is concerned with a blend of cocoamidopropyl betaine and oleamidopropyl betaine which have thickening and foam boosting properties and maintain the required viscosity on combination with ingredients conventionally used in cosmetic formulations such as hair and skin care products.

In one aspect of the invention, cocoamidopropyl betaine (CB) and oleamidopropyl betaine (OB) are combined in ratios of from about 1:4 to about 3:2 of CB to OB. At ratios of higher than 3:2, the blends tend to gel and become more difficult to solubilize.

In another aspect, blends of CB and OB are incorporated in cosmetic formulations such as conventional hair and skin care formulations, for instance shampoos and soaps, particularly soft soaps.

In yet another aspect of the invention, the blends of CB and OB are incorporated in cosmetic formulations containing rich emollients such as Jojoba oil, sweet almond oil and Vitamin E. The CB/OB blends of the invention are capable of incorporating larger amounts of such emollients without adverse effect to the viscosity of the formulation. Generally, prior art formulations contain about 0.1% Jojoba oil. The present blends of betaines can efficiently emulsify up to about 0.5% Jojoba oil.

The CB/OB blends of the invention are generally present in amounts of from about 5 to 30% by weight based on the total cosmetic composition. Shampoos and liquid soaps generally contain about 5 to 10% by weight and bath gels generally contain about 10 to 30% by weight of the CB/OB blends.

The cosmetic formulations comprise a suitable cosmetic carrier. The composition of the carrier depends on the purpose for which the final composition is intended. Thus, different carriers will be used dependent on whether the composition is to be used as a shampoo, a soap etc. These carriers are as described in the art. They may contain surfactants such as sodium lauryl sulfate, sodium lauryl ether sulfate, sodium lauryl sarcosinate, lauroamphocarboxyglycinate or co-coamphocarboxyglycinate, solvents such as glycol and propylene glycol, proteins, citric acid, coloring agents, preservatives, fragrances, mineral oils, thickeners such as sodium chloride, PEG 6000 distearate, PEG 80 sorbitan laurate, cocamide DEA, lauramide DEA or hydroxypropyl methylcellulose, vitamins, silicones, emollients such as lanolin, isopropyl palmitate, isopropyl myristate or petrolatum and viscosity builders such as carageenan, carbomers or cocamidopropyl hydroxy sultaine.

The following examples serve to illustrate the invention but they are not intended to limit the scope of the invention.

EXAMPLE I

The following shampoo formulations were prepared using the blend of the invention comprising CB and OB in a ratio of 1:1 in formulation B and comparing this with formulations A and C outside the scope of the invention. The pH of each formulation is adjusted to 7.0. Miranol® 2MCAS MODIFIED is a mixture of the lauryl sulfate and laureth-3 sulfate salts of a dicarboxymethylated derivative of a cocoimidazoline.

| CONDITIONING SHAMPOO | | | |
|---|---|---|---|
| | A | B | C |
| Alfa Olefin Sulfonate (40%) | 15.0 | 15.0 | 15.0 |
| MIRANOL 2MCAS MODIFIED | 15.0 | 15.0 | 15.0 |
| CB | 15.0 | — | — |
| CB/OB | — | 15.0 | — |
| Cocamide Diethanolamine (D.E.A.) | 2.0 | 2.0 | 2.0 |
| Aloe Vera | 7.5 | 7.5 | 7.5 |
| Water | 45.5 | 45.5 | 60.5 |

The viscosities were measured Brookfield viscometer Model LVT with spindle #4 at 12 rpm after one minute at 25° C. in this Example and the following Examples.

| Formulation | Viscosity |
|---|---|
| A | 22,500 cps |
| B | 35,000 cps |
| C | less than 50 cps |

The viscosity results show CB/OB to provide a better thickening effect than cocoamidopropyl betaine. Cocoamidopropyl betaine and CB/OB were shown to be equivalent in foam boosting property.

EXAMPLE II

Cedepal TD 404M in the following soap formulation is sodium tridecyl ether sulfate (3 moles of ethylene oxide).

| SOFT SOAP | | | |
|---|---|---|---|
| | A | B | C |
| Alfa Olefin Sulfonate (40%) | 15.0 | 15.0 | 15.0 |
| CEDEPAL ® TD 404 M | 10.0 | 10.0 | 10.0 |
| CB | 20.0 | — | — |
| CB/OB | — | 20.0 | — |
| Lauric Diethanolamide | — | — | — |
| Superamide ® L9C | 2.5 | 2.5 | 2.5 |
| Glycol Stearate-Cerasynt ® IP (Opacifier) | 1.0 | 1.0 | 1.0 |
| Preservative-Glydant ® (DM DM Hydantoin) | 0.2 | 0.2 | 0.2 |
| NaCl | 1.0 | 1.0 | 1.0 |
| Water | 50.3 | 50.3 | 70.3 |

The pH of each soap formulation is adjusted to 7.0.

| Formulation | Viscosity |
|---|---|
| A | 23,000 cps |
| B | 29,000 cps |

-continued

| Formulation | Viscosity |
| --- | --- |
| C | less than 50 cps |

The same results as above in the shampoo evaluations as to viscosity and foam boosting effect were observed.

The results thus show that the best increase in viscosity properties is obtained with CB/OB.

EXAMPLE III

This example shows effective incorporation of 0.2% Jojoba oil when using CB/OB in a ratio of 1:1. Cocoamidopropyl betaine (CB) alone is also capable of effective incorporation of the oil but results in a formulation of unsatisfactory viscosity.

Miranol C2M N.P is a disodium salt of carboxymethylated 2-cocoyl-1-hydroxyethyl-4,5-dihydro imidazoline derivatives. The CTFA name is cocoamphocarboxyglycinate.

| JOJOBA OIL SHAMPOO | | | |
| --- | --- | --- | --- |
|  | A | B | C |
| MIRANOL ® 2MCAS-Modified | 18.0 | 18.0 | 18.0 |
| MIRANOL ® C2M Conc. N.P. | 10.0 | 10.0 | 10.0 |
| CB/OB (1:1) | 15.0 | — | — |
| CB | — | 15.0 | — |
| MIRATAINE ® ODMB-35 | — | — | 15.0 |
| Witcamide 82 (Cocamide DEA)* | 3.5 | 3.5 | 3.5 |
| JOJOBA OIL | 0.2 | 0.2 | 0.2 |
| Herbal Extract | 0.1 | 0.1 | 0.1 |
| Water | 53.2 | 53.2 | 53.2 |

The pH is adjusted to 7.0 for all formulations.

| Formulation | Viscosity |
| --- | --- |
| A | 18,500 cps |
| B | 6,000 cps |
| C | —(separation) |

*CTFA designation

EXAMPLE IV

The example demonstrates effective incorporation of 0.5% Jojoba oil when using either CB/OB or CB alone.

The first product is clear and has a higher viscosity than the second which is hazy.

| JOJOBA OIL SHAMPOO | | |
| --- | --- | --- |
|  | A | B |
| MIRANOL ® 2MCAS-Mod. | 18.0 | 18.0 |
| MIRANOL ® C2M Conc. N.P. | 10.0 | 10.0 |
| CB/OB (1:1) | 15.0 | — |
| CB | — | 15.0 |
| WITCAMIDE 82 (Cocamide DEA)* | 5.0 | 5.0 |
| Lanoquat 50 (Quaternium 33 + Ethyl Hexanediol)* | 1.0 | 1.0 |
| JOJOBA OIL | 0.5 | 0.5 |
| Herbal extract | 0.1 | 0.1 |
| Water | 50.4 | 50.4 |

Adjust pH to 7.0

| Formulation | Viscosity |
| --- | --- |
| A | 2,500 cps (clear) |
| B | 1,000 cps (hazy) |

*CTFA designation

What is claimed is:

1. A composition suitable for use in hair and skin care cosmetic formulations which comprises a blend of cocoamidopropyl betaine and oleamidopropyl betaine in a ratio of from about 1:4 to about 3:2.

2. A composition according to claim 1, wherein the ratio of coccamidopropyl betaine to oleamidopropyl betaine is 1:1.

3. A cosmetic composition which comprises a carrier which is suitable for use in hair care and skin care formulations which contains a blend of cocoamidopropyl betaine and oleamidopropyl betaine in a ratio of from about 1:4 to about 3:2.

4. A cosmetic composition according to claim 3, which comprises an emollient.

5. A cosmetic composition according to claim 4, wherein said emollient is Jojoba oil or sweet almond oil.

6. A cosmetic composition according to claim 3, wherein said cosmetic carrier is suitable for hair care formulations.

7. A cosmetic composition according to claim 4, wherein said blend of cocoamidopropyl betaine and oleamidopropyl betaine is present in an amount of from about 5 to 30% by weight of the total composition.

* * * * *